United States Patent [19]

Malherbe

[11] Patent Number: 4,472,547

[45] Date of Patent: Sep. 18, 1984

[54] N-PIPERIDYL LACTAM LIGHT STABILIZERS

[75] Inventor: Roger F. Malherbe, Yonkers, N.Y.

[73] Assignee: Ciba-Geigy Corporation, Ardsley, N.Y.

[21] Appl. No.: 544,309

[22] Filed: Oct. 21, 1983

Related U.S. Application Data

[63] Continuation-in-part of Ser. No. 509,102, Jun. 30, 1983.

[51] Int. Cl.$^3$ ................. C07D 401/00; C08K 5/34
[52] U.S. Cl. ...................... 524/98; 524/102; 546/187; 546/208
[58] Field of Search ............... 524/98, 102; 546/187, 546/208

[56] References Cited

U.S. PATENT DOCUMENTS

| | | | |
|---|---|---|---|
| 3,000,880 | 9/1961 | Phillips | 260/239.3 A |
| 3,684,765 | 8/1972 | Matsui et al. | 524/99 |
| 3,850,877 | 11/1974 | Cook | 524/99 |
| 4,014,887 | 3/1977 | Randell et al. | 524/99 |
| 4,033,928 | 7/1977 | Randell et al. | 523/451 |
| 4,309,541 | 1/1982 | Werner | 546/16 |
| 4,309,546 | 1/1982 | Karrer | 546/187 |
| 4,340,534 | 7/1982 | Wiezer et al. | 524/102 |
| 4,356,307 | 10/1982 | Kelkenberg et al. | 524/102 |
| 4,371,644 | 2/1983 | Soma et al. | 524/102 |

OTHER PUBLICATIONS

H. J. Heller et al. Pure and Applied Chemistry, 36, 141–161, (1973).

*Primary Examiner*—John Kight, III
*Assistant Examiner*—Kriellion Morgan
*Attorney, Agent, or Firm*—Luther A. R. Hall

[57] ABSTRACT

Compounds of the formula $(L-T)_g-E$ (I) or $(L-T-G)_h-Q$ (II), where L is a lactam group, T is a substituted 4-piperidinyl hindered amine moiety and E or Q are selected linking or terminal groups, are effective light stabilizers for polyolefins and other organic polymers.

26 Claims, No Drawings

N-PIPERIDYL LACTAM LIGHT STABILIZERS

This is a continuation-in-part of application Ser. No. 509,102, filed on June 30, 1983.

BACKGROUND OF THE INVENTION

The present invention pertains to compounds containing a lactam group in combination with a substituted 4-piperidinyl hindered amine moiety which are useful as light and heat stabilizers for organic materials and to stabilized compositions containing said compounds.

The hindered amine compounds having the 2,2,6,6,-tetrasubstituted piperidinyl structure have long been known as effective light stabilizers for organic materials and have enjoyed considerable commercial success.

Such hindered amine light stabilizers are described in detail by H. J. Heller and H. R. Blattmann, Pure and Applied Chemistry, 36, 141–161 (1973).

It is known from U.S. Pat. Nos. 3,850,877 and 4,033,928 that esters and amides of substituted 2,2,6,6-tetramethylpiperidine are good light stabilizers for polymeric substrates, particularly polyolefins and epoxy resins.

U.S. Pat. No. 4,309,546 describes substituted N-piperidin-4'-yl-2-pyrrolidone-4-carboxylic acid derivatives of formula

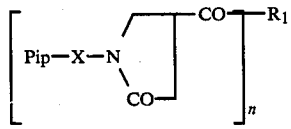

where n is 1–4, $R_1$ is hydroxyl, alkoxy, amino or substituted amino, X is a direct bond or linking group and Pip is substituted or unsubstituted 2,2,6,6-tetraalkylpiperidn-4-yl. These compounds are useful as light stabilizers.

Although structurally the instant compounds are somewhat related to the compounds of U.S. Pat. No. 4,309,546, the instant compounds possess better solubility characteristics, and exhibit superior thermal and particularly superior hydrolytic stability compared to said compounds.

DETAILED DISCLOSURE

This invention relates to compounds containing a lactam group in combination with a substituted 4-piperidinyl hindered amine moiety which are useful as light stabilizers for organic polymers and to stabilized compositions containing said compounds.

The instant invention more particularly pertains to a light stabilizer compound of the formula I or II $$(L—T)_g—E \qquad (I)$$

$$(L—T—G)_h—Q \qquad (II)$$

wherein
L is a lactam group of the formula

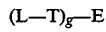
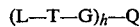
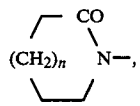

n is 0 to 3,
T is a group of the formula

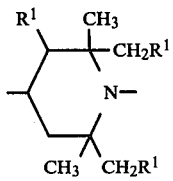

with
L attached to the 4-position of the piperidinyl ring,
$R^1$ is hydrogen or alkyl of 1 to 5 carbon atoms,
g is 1 or 2,
when g is 1,
E is hydrogen, oxygen, hydroxyl, alkyl of 1 to 12 carbon atoms, alkenyl of 3 to 8 carbon atoms, propargyl, benzyl, cyano, hydroxyalkyl of 2 to 4 carbon atoms, alkanoyl of 2 to 10 carbon atoms, alkenoyl of 3 to 4 carbon atoms, benzoyl, alkoxy of 1 to 8 carbon atoms, alkanoyloxy of 2 to 10 carbon atoms, alkenoyloxy of 3 to 4 carbon atoms, benzoyloxy,
when g is 2,
E is a straight- or branched- chain alkylene of 2 to 6 carbon atoms, styrolene, 2-butenylene or alkylenearylenealkylene of 8 to 15 carbon atoms; or
G is $G_1$ or $G_2$,
$G_1$ is

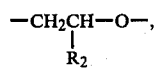

$R^2$ is hydrogen, alkyl of 1 to 2 carbon atoms or phenyl,
$G_2$ is —$CH_2COO$—,
where
T is attached to the methylene carbon atom of $G_1$ or $G_2$,
h is 1 to 4,
when h is 1 and G is $G_1$,
Q is alkanoyl of 2 to 10 carbon atoms, benzoyl, or the group

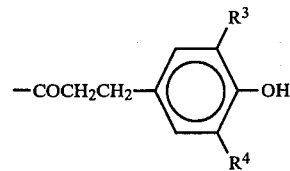

$R^3$ is alkyl of 1 to 8 carbon atoms,
$R^4$ is branched alkyl of 3 to 8 carbon atoms,
when h is 2 and G is $G_1$,
Q is carbonyl, oxalyl or alkanedioyl of 3 to 12 carbon atoms,
when h is 3 and G is $G_1$,
Q is alkanetrioyl of 6 to 10 carbon atoms,
when h is 4 and G is $G_1$,
Q is alkanetetroyl of 8 to 12 carbon atoms,
when h is 1 and G is $G_2$,
Q is alkyl of 1 to 12 carbon atoms, or the group T-E 10 where E is as defined above when g is 1,
when h is 2 and G is $G_2$, Q is alkylene of 2 to 12 carbon atoms, cycloalkylene of 6 to 8 carbon atoms, 3-oxapentamethylene, 1,4-cyclohexylenedimethylene or the group —T—CH$_2$CH$_2$—, when h is 3 and G is G$_2$, Q is alkanetriyl of 3 to 8 carbon atoms, or when h is 4 and G is G$_2$, Q is alkanetetrayl of 4 to 10 carbon atoms.

The instant compounds each have at least one lactam group L of formula

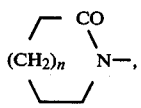

where n is 0 to 3. When n is 0, L is a pyrrolidone; when n is 1, L is a delta-valerolactam; when n is 2, L is an epsilon-caprolactam; and when n is 3, L is a zeta-oenantholactam. Preferably n is 2 or 3, and most preferably n is 2.

T is the divalent radical derived from a substituted piperidin-4-ol where R$^1$ is hydrogen or alkyl of 1 to 5 carbon atoms such as, for example, methyl, ethyl, n-butyl or n-amyl. Preferably R$^1$ is hydrogen or methyl, and most preferably R$^1$ is hydrogen.

When g is 1, E may be hydrogen, oxygen, hydroxyl or alkyl of 1 to 12 carbon atoms such as, for example, methyl, ethyl, isopropyl, sec-butyl, n-amyl, 2-ethylhexyl, n-decyl or n-dodecyl, preferably alkyl of 1 to 4 carbon atoms.

E may also be alkenyl of 3 to 8 carbon atoms such as, for example, allyl, butenyl, crotyl or octenyl, preferably allyl.

When E is hydroxyalkyl, E is, for example, 2-hydroxyethyl, 2-hydroxypropyl or 2-hydroxybutyl, preferably 2-hydroxyethyl.

E is alkanoyl of 2 to 10 carbon atoms such as, for example, acetyl, propionyl, butanoyl, valeroyl, caproyl, capryloyl or decanoyl. Preferably E as alkanoyl is acetyl.

E is also alkenoyl of 3 or 4 carbon atoms such as, for example, acryloyl, methacryloyl or crotonoyl.

When E is alkoxy of 1 to 8 carbon atoms, E is, for example, methoxy, ethoxy, isopropoxy, n-butoxy, hexyloxy or octyloxy.

When E is alkanoyloxy of 2 to 10 carbon atoms, E is, for example, acetoxy, propionyloxy, butanoyloxy, valeroyloxy, octanoyloxy or decanoyloxy.

When E is alkenoyloxy of 3 to 4 carbon atoms, E, is, for example, acryloyloxy, methacryloyloxy or crotonyloxy.

Preferably when g is 1, E is hydrogen, oxygen, hydroxyl, alkyl of 1 to 4 carbon atoms, allyl, 2-hydroxyethyl, acetyl, propargyl, benzyl, cyano, benzoyl or benzoyloxy.

When g is 2, E is a straight- or branched-chain alkylene of 2 to 6 carbon atoms such as, for example, ethylene, trimethylene, 1,2-propylene, 1,2-butylene, tetramethylene, pentamethylene or hexamethylene. Preferably E is ethylene.

When g is 2, E is also styrolene or alkylenearylenealkylene of 8 to 15 carbon atoms such as, for example, p-xylylene.

Preferably when g is 2, E is ethylene or p-xylylene.

R$^2$ is hydrogen, methyl, ethyl or phenyl, preferably hydrogen.

When Q is alkanoyl of 2 to 10 carbon atoms, Q is, for example, acetyl, propionyl, butanoyl, valeroyl, caproyl, capryloyl or decanoyl, preferably acetyl.

R$^3$ is alkyl of 1 to 8 carbon atoms such as, for example, methyl, isopropyl, tert-butyl, tert-amyl or tert-octyl. Preferably R$^3$ is alkyl of 4 to 8 carbon atoms, most preferably tert-butyl.

R$^4$ is branched alkyl of 3 to 8 carbon atoms such as, for example, isopropyl, tert-butyl, tert-amyl or tert-octyl. Preferably R$^4$ is tert-butyl.

When Q is alkanedioyl of 3 to 12 carbon atoms, Q is, for example, malonyl, succinyl, adipoyl, suberoyl, sebacoyl or dodecanoyl. Preferably Q is alkanedioyl of 6 to 10 carbon atoms.

Q is also alkanetrioyl of 6 to 10 carbon atoms such as, for example, tricarballyloyl or citroyl.

Q is also alkanetetraoyl of 8 to 12 carbon atoms such as, for example, 1,2,3,4-butanetetracarboxoyl.

When Q is alkyl of 1 to 12 carbon atoms, Q has the same meanings as does E when g is 1 and E is alkyl.

Preferably when h is 1 and G is G$_2$, Q is alkyl of 1 to 4 carbon atoms or the group T-E.

When Q is alkylene of 2 to 12 carbon atoms, Q is, for example, ethylene, 1,2-propylene, trimethylene, tetramethylene, pentamethylene, hexamethylene, octamethylene, decamethylene or dodecamethylene.

When Q is cycloalkylene of 6 to 8 carbon atoms, Q is, for example, 1,2-cyclohexylene, 1,3-cyclohexylene or 1,4-cyclohexylene.

When h is 2 and G is G$_2$, Q is preferably alkylene of 2 to 8 carbon atoms or the group —T—CH$_2$CH$_2$—.

When Q is alkanetriyl of 3 to 8 carbon atoms, Q is, for example, glyceryl, 1,2,4-butanetriyl or the radical derived from 1,1,1-trimethylolethane, 1,1,1-trimethylolpropane or 1,1,1-trimethylolbutane.

Q is also alkanetetrayl of 4 to 10 carbon atoms such as, for example, neopentanetetrayl (pentaerythrityl).

The intermediates needed to prepare the instant compounds are largely items of commerce or are easily prepared by known methods.

U.S. Pat. No. 3,000,880 teaches that epsilon-caprolactone reacts with a primary amine in an aqueous medium to give N-alkyl-epsilon-caprolactams. This reaction proceeds at high pressures and at temperatures above the critical temperature of water.

In order to protect the 4-amino-2,2,6,6-tetraalkylpiperidine from such rigorous reaction conditions, an alternative process was used to prepare the instant lactams in two simple steps.

1. Hydrogenation of triacetoneamine (2,2,6,6-tetramethyl-4-piperidone) or other tetraalkyl-4-piperidones in the presence of an appropriate aminoalkanoic acid, such as 6-aminocaproic acid, yields the corresponding N-piperidyl amino acid.

2. Cyclization of the amino acid to the corresponding N-piperidyl lactam occurs when the amino acid is heated to a temperature of about 260°–270° C. under nitrogen with water being liberated.

Acid catalysts such as phosphoric acid, p-toluenesulfonic acid or trichloroacetic acid can also be used to aid the cyclization reaction.

The preparation of the intermediate 4-hydroxypiperidines is taught in U.S. Pat. No. 4,014,887 and of the 4-aminopiperidines in U.S. Pat. No. 3,684,765.

The compounds of this invention are effective light stabilizers in a wide range of organic polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.
2. Mixtures of the homopolymers cited under (1), for example mixtures of polypropylene and polyethylene, polypropylene and polybutene-1, polypropylene and polyisobutylene.
3. Copolymers of the monomers based on the homopolymers cited under (1), for example ethylene/propylene copolymers, propylene/butene-1, copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.
4. Polystyrene.
5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.
6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.
7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.
8. Polymers which are derived from $\alpha,\beta$-unsaturated acids and derivatives thereof, such as polyacrylates and polymethacrylates, polyacrylic amides and polyacrylonitrile.
9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.
10. Homopolymers and copolymers which are derived from epoxides, for example polyethylene oxide or the polymers which are derived from bis-glycidyl ethers.
11. Polyacetals, for example polyoxymethylene, as well as polyoxymethylenes which contain ethylene oxide as comonomer.
12. Polyalkylene oxides, for example polyoxyethylene, polypropylene oxide or polybutylene oxide.
13. Polyphenylene oxides.
14. Polyurethanes and polyureas, such as in urethane coatings.
15. Polycarbonates.
16. Polysulfones.
17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.
18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.
19. Cross-linked polymers which are derived from aldehydes on the one hand and from phenols, ureas and melamine on the other, for example phenol/formaldehyde, urea/formaldehyde and melamine/formaldehyde resins.
20. Alkyd resins, for example glycerol/phthalic acid resins and mixtures thereof with melamine/formaldehyde resins.
21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.
22. Natural polymers, for example cellulose, rubber, as well as the chemically modified homologous derivatives thereof, for example cellulose acetates, cellulose propionates and cellulose butyrates and the cellulose ethers, for example methyl cellulose.

The stabilizing of polyolefins, styrene polymers and polyamides and of polyurethanes is of particular importance, and the instant copolymers are outstandingly suitable for this. Examples of such polymers are high density and low density polyethylene, polypropylene, ethylene/propylene copolymers, polystyrene, styrene/butadiene/acrylonitrile terpolymers, mixtures of polyolefins or of styrene polymers, and polyurethanes based on polyethers or polyesters, in the form of lacquers, filaments, films, sheets, elastomers or foams.

The instant stabilizers are added to the plastics in a concentration of 0.05 to 5% by weight, calculated relative to the material to be stabilized. Preferably, 0.1 to 2.5% by weight of the stabilizer calculated relative to the material to be stabilized, is incorporated into the latter.

Incorporation can be effected after polymerization, for example by mixing the compounds and, if desired, further additives into the melt by the methods customary in the art, before or during shaping, or by applying the dissolved or dispersed compounds to the polymer, with subsequent evaporation of the solvent if necessary.

The stabilizers can also be added to the plastics to be stabilized in the form of a master batch which contains these compounds, for example in a concentration of 2.5 to 25% by weight.

Although the compounds of the invention may be used to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.05 to about 5% by weight of the stabilized composition, although this will vary with the particular substrate and application. An advantageous range is from about 0.1 to about 2.5%.

The stabilizers of Formula I or II may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.05 to about 5%, preferably from about 0.1 to about 2.5% by weight of various conventional additives, such as the following, particularly phenolic antioxidants or light-stabilizers, or mixtures thereof:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulfide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6-(-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl]2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethyl-benzene, 1,4-di-(3,5-di-tert-butyl-4-hydroxybenzyl)-2,3,5,6-tetramethylbenzene and 2,4,6-tri-(3,5-di-tert.-butyl-4-hydroxy-benzyl)-phenol.

1.8 s-Triazine compounds, such as for example 2,4-bis-octylmercapto-6-(3,5-di-tert.-butyl-4-hydroxyanilino)-s-triazine, 2-octylmercapto-4,6-bis-(3,5-di-tert.-butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acids, such as, for example 1,3,5-tris-(3,5,-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine, N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol;. 1,9-nonanediol, ethylene glycol, 1,2-propane-diol, diethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenyl)propionic acid with monohydric or polyhydric alcohols, such as for example, with methanol, ethanol, octadecanol, 1,6-hexanediol, 1-9-nonanediol, ethylene glycol, 1,2propanediol, diethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]-octane, especially the tetrakis ester of pentaerythritol.

1.13 Benzylphosphonates, such as, for example, dimethyl 3,5 di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butylphenyl ester.

2.2 Sterically hindered amines e.g., 4-benzoyl-2,2,6,6-tetramethylpiperidine, 4-stearyloxy-2,2,6,6-tetramethylpiperidine, bis-(2,2,6,6-tetramethylpiperidyl) sebacate, bis-(1,2,2,6,6-pentamethylpiperidyl) sebacate, bis-(1,2,2,6,6-pentamethylpiperidyl) 2-n-butyl-2-(2-hydroxy-3,5-di-tert-butylbenzyl)malonate or 3-n-octyl-7,7,9,9-tetra-methyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.butyl-oxanilide, 2,2'-didodecycloxy-5,5'-di-tert.-butyl-oxanilide, 2-ethoxy-2'-ethyloxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.- butyl-oxanilide, or mixture of ortho- and para-methoxy- as well as of o- and p-ethoxy-di-substituted oxanilides.

3. Metal deactivators, e.g., oxanilide, isophthalic acid dihydrazide, sebacic acid-bis-phenylhydrazide, bis-benzylidene-oxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide. 4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyl-dialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl) diphenylene-4,4'-bis(phosphonite).

Other additives that can be incorporated in the stabilized compositions are thiosynergists such as dilauryl thiodioprionate, lubricants such as stearyl alcohol, fillers, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

EXAMPLE 1

N-(2,2,6,6-Tetramethylpiperidin-4-yl)-epsilon-caprolactam (a) A solution of 212 g (1.34 mole) of triacetoneamine (2,2,6,6-tetramethyl-4-piperidone) and 175 g (1.34 mole) of 6-aminocaproic acid in 600 ml of water is placed in a 1-liter jacketed autoclave fitted with a stirrer, hydrogen inlet and thermometer. To the solution is then added 1.25 g of platinum oxide hydrogenation catalyst and catalytic hydrogenation is carried out at 3 atmospheres pressure at 25° C. till the theoretical amount of hydrogen is absorbed.

The catalyst is then removed by filtration and the filtrate is concentrated by in vacuo evaporation to give the intermediate, N-(2,2,6,6-tetramethylpiperidin-4-yl)-6-aminocaproic acid, in a yield of 285 g as a white crystalline solid melting at 221°–223° C.

(b) To a 500-ml flask fitted with a stirrer, heating mantle and nitrogen inlet tube is added 100 g (0.34 mole) of N-(2,2,6,6-tetramethylpiperidin-yl)-6-aminocaproic acid. A stream of nitrogen is provided and the acid is heated for two hours at 265° C. under nitrogen till the evolution of water ceases. The reaction flask is then cooled to 110° C. and 300 ml of heptane is added to cover the crude product. The mixture is stirred to dissolve most of the product. The insoluble residue is removed by filtration and the above-named product is obtained as a white crystalline material upon cooling the filtrate in a yield of 70.1 g, melting at 113°–117° C.

IR(CHCl$_3$): $\nu_{C=O}$ 1626 cm$^{-1}$

Analysis $C_{15}H_{28}N_2O$ (252.40): Calc: C, 71.38; H, 11.18; N, 11.10. Found: C, 71.59; H, 11.28; N, 11.14.

EXAMPLE 2

N-(2,2,6,6-Tetramethylpiperidin-4-yl)-zeta-oenantholactam a. Following the method of Example 1a, but using an equivalent amount of 7-aminoheptanoic acid in place of 6-aminocaproic acid, N-(2,2,6,6-tetramethylpiperidin-4-yl)-7-aminoheptanoic acid is obtained as a white solid, melting at 162°–165° C.

b. Following the general procedure of Example 1b, 50 g (0.176 mole) of N-(2,2,6,6-tetramethylpiperidin-4-yl)-7-aminoheptanoic acid is heated at 300° C. in the presence of 0.1 g of p-toluenesulfonic acid dehydration catalyst. The crude product is first vacuum distilled at 155°–160° C./0.01 mm to give 9.9 g of the above named product. The distilled product is further purified by recrystallization from heptane to give a solid melting at 87°–89° C.

Analysis $C_{16}H_{30}N_2O$ (266.4): Calc: C, 72.13; H, 11.35; N, 10.51. Found: C, 71.7; H, 11.1; N, 10.5.

EXAMPLE 3

N-(1,2,2,6,6-Pentamethylpiperidin-4-yl)-epsilon-caprolactam

A solution of 63.0 g (0.25 mole) of N-(2,2,6,6-tetramethylpiperidin-4-yl)-epsilon-caprolactam, prepared in Example 1, in 150 ml of toluene is added to a flask fitted with a reflux condenser, stirrer and thermometer. To this solution is then added a second solution of 28.5 ml (0.30 mole) of dimethyl sulfate in 100 ml of toluene. The mixture is heated for one hour at 80° C. and then 50 ml of concentrated ammonium hydroxide is added.

The upper toluene layer is separated and dried over potassium carbonate. Removal of the toluene by vacuum distillation gives the above named product as a white powder, melting at 76°–79° C.

Analysis $C_{16}H_{30}N_2O$ (266.4): Calc: C, 72.13; H, 11.35; N, 10.51. Found: C, 71.8; H, 11.2; N, 10.4.

EXAMPLE 4

N-(1-Allyl-2,2,6,6-tetramethylpiperidin-4-yl)-epsilon-caprolactam

Following the general procedure of Example 3, 12.1 g (0.05 mole) of the compound prepared in Example 1 is dissolved in 75 ml of N,N-dimethylformamide containing a suspension of 10.6 g (0.1 mole) of sodium carbonate. To this mixture is then added 14.6 g (0.05 mole) of allyl bromide and the reaction mixture is then heated at 80° C. for two hours. The solvent is then removed in vacuo and the residue is vacuum distilled at 171°–176° C./0.7 mm to give 7.6 g of the above named product.

EXAMPLE 5

N-(1Propargyl-2,2,6,6-tetramethylpiperidin-4-yl)-epsilon-caprolactam

The above-named product is obtained when, using the procedure of Example 4, an equivalent amount of propargyl bromide is substituted for allyl bromide. The product is vacuum distilled at 153°–160° C./0.04 mm giving a liquid which crystallized on standing to a solid melting at 105°–109° C.

Analysis $C_{18}H_{32}N_2O$ (292.5): Calc: C, 74.4 H, 10.4; N, 9.6. Found: C, 74.3; H, 10.2; N, 9.7.

EXAMPLE 6

N-(1-Benzyl-2,2,6,6-tetramethylpiperidin-4-yl)-epsilon-caprolactam

The above-named product is obtained according to the procedure of Example 4 when an equivalent amount of benzyl chloride is substituted for allyl bromide.

The crude product is recrystallized from methanol:water (4:1) to give a solid melting at 126°–127° C.

Analysis $C_{22}H_{34}N_2O$ (342.5): Calc: C, 77.2; H, 10.0; N, 8.2. Found: C, 77.4; H, 10.1; N, 8.0.

EXAMPLE 7

N,N'-p-Xylylene-bis[4-(2-oxo-1-azepinyl)-2,2,6,6-tetramethylpiperidine]

The above-named compound is prepared according to the method of Example 4 using an appropriate amount of p-xylylene dichloride in place of allyl bromide.

The crude product obtained is recrystallized from a mixture of heptane and methylene chloride to give a white powder melting at 280°–283° C.

Analysis: $C_{38}H_{62}N_4O_2$ (607.0): Calc: C, 75.2 H, 10.3; N, 9.2. Found: C, 75.0 H, 9.9 N, 9.1.

EXAMPLE 8

N-(1-Cyano-2,2,6,6-tetramethylpiperidin-4-yl)-epsilon-caprolactam

The above named compound is made by the general procedure of Example 4 when an equivalent amount of cyanogen chloride is substituted for allyl bromide.

The compound is obtained as a white solid melting at 168°–169° C. after recrystallization from acetone-water.

Analysis: $C_{16}H_{27}N_3O$ (277.41): Calc: C, 69.3; H, 9.8; N, 15.1. Found: C, 69.1; H, 9.7; N, 15.0.

EXAMPLE 9

N-(1-Acetyl-2,2,6,6-tetramethylpiperidin-4-yl)-epsilon-caprolactam

A solution of 50.5 g (0.2 mole) of N-(2,2,6,6-tetramethylpiperidin-4-yl)-epsilon-caprolactam, prepared in Example 1, in 102 g of acetic anhydride with 0.2 g of sulfuric acid catalyst is heated for four hours at 120° C. At the end of this period the excess acetic anhydride is removed in vacuo. The residue is then dissolved in 200 ml of methylene chloride, washed thrice with 100 ml portions of water, then with 10% aqueous sodium bicarbonate and finally dried over anhydrous magnesium sulfate. The solvent is allowed to evaporate to give a crude product which when recrystallized from toluene:hexane (1:3) yields 38.4 g of white solid melting at 104°–108° C.

Analysis $C_{12}H_{32}N_2O_2$ (296.45): Calc: C, 68.88; H, 10.88; N, 9.45. Found: C, 69.2; H, 10.5; N, 9.5.

EXAMPLE 10

N-[1-(2-Hydroxyethyl)-2,2,6,6-tetramethylpiperidin-4-yl]-epsilon-caprolactam To a small autoclave is charged a solution of 6.6 g (0.15 mole) of ethylene oxide and 25.2 g (0.1 mole) of N-(2,2,6,6-tetramethylpiperidin-4-yl)-epsilon-caprolactam, in 100 ml of N,N-dimethylformamide. The autoclave is heated for four hours at 190° C. during which time the pressure dropped from 100 psi (7 kg/cm²) to 70 psi (4.9 kg/cm²). The reaction mixture is then distilled in vacuo (50° C./2 mm) to remove the solvent. The residue is crystallized from 300 ml of heptane:toluene (2:1) to give the above-named product in a yield of 13.7 g as a white solid melting at 141°–142° C.

Analysis $C_{17}H_{32}N_2O_2$ (296.5) Calc: C, 68.9; H, 10.9; N, 9.4. Found: C, 68.8; H, 11.0; N, 9.2.

EXAMPLE 11

Di-[2-[4-(2-oxo-1-azepinyl)-2,2,6,6-tetramethylpiperidin-1-yl]-ethyl] Adipate To a solution of 7 g (0.236 mole) of the compound prepared in Example 10 and 2 g (0.115 mole) of dimethyl adipate in 50 ml of xylene is added 50 mg of lithium amide esterification catalyst. The reaction mixture is heated to 140° C. and the xylene solvent is distilled off over a six-hour period. The resulting residue is crystallized from heptane:toluene (2:1) to give the above-named compound in a yield of 4.9 g as a white solid melting 159°–160° C.

Analysis $C_{40}H_{70}N_4O_6$ (703.0): Calc: C, 68.3; H, 10.0; N, 8.0. Found: C, 67.3; H, 10.2; N, 7.7.

EXAMPLE 12

Di-[2-[4-(2-oxo-1-azepinyl)-2,2,6,6-tetramethylpiperidin-1-yl]-ethyl] Sebacate The above-named compound is prepared following the procedure of Example 11 when an equivalent amount of dimethyl sebacate is used in lieu of dimethyl adipate. The compound is prepared as white crystals from heptane which melt at 104°–111° C.

Analysis $C_{44}H_{78}N_4O_6$ (759.1): Calc: C, 69.6; H, 10.4; N, 7.4. Found: C, 69.7; H, 10.0; N, 7.2.

EXAMPLE 13

2-[4-(2-Oxo-1-azepinyl)-2,2,6,6-tetramethylpiperidin-1-yl]-ethyl 4-Hydroxy-3,5-di-tert-butylhydrocinnamate The above-named product is obtained by the method of Example 11 when an appropriate amount of methyl 4-hydroxy-3,5-di-tert-butylhydrocinnamate is used instead of dimethyl adipate. The crude product is recrystallized from xylene: heptane (2:1) to give the desired compound as a white solid melting at 159°–161° C.

Analysis $C_{34}H_{56}N_2O_4$ (556.8): Calc. C, 73.3; H, 10.1; N, 5.0. Found: C, 73.1; H, 10.2; N, 5.1.

EXAMPLE 14

N-(1-Oxyl-2,2,6,6-tetramethylpiperdin-4-yl)-epsilon-caprolactam

To a solution of 25.4 g (0.1 mole) of the lactam compound prepared in Example 1 in 200 ml of chloroform is added portionwise 38 g (0.22 mole) of m-chloroperbenzoic acid over a one-hour period. The reaction mixture is stirred for an eighteen-hour period at ambient temperature. The mixture is then filtered to remove the m-chlorobenzoic acid formed. The filtrate is washed successively with 1N sulfuric acid, with water and with 10% aqueous sodium bicarbonate and then dried. The solvent is removed in vacuo and the residue recrystallized from tolueneheptane to give the above-named compound as an orange solid melting at 158°–164° C.

The NMR spectrum confirmed the presence of a paramagnetic species (free radical) in the product.

EXAMPLE 15

N-(1-Hydroxy-2,2,6,6-tetramethylpiperidin-4-yl)-epsilon-caprolactam

In a small hydrogenation autoclave is added a solution of 26.7 g (0.1 mole) of the oxyl compound prepared in Example 14 dissolved in 250 ml of dioxane along with 0.8 g of 5% palladium-on-charcoal hydrogenation catalyst. The reaction mixture is stirred for a period of four hours at a temperature of 25° C. under hydrogen till the theoretical amount of hydrogen is absorbed. The reaction mixture is then heated to 100° C. and the catalyst removed by filtration from the heated mixture. The filtrate is cooled to give the above-named product in a yield of 18.7 g melting at 212°–215° C.

Analysis $C_{15}H_{28}N_2O_2$ (268.39): Calc: C, 67.12; H, 10.52; N, 10.44. Found: C, 67.1; H, 10.0; N, 10.4.

EXAMPLE 16

N-(1-Benzoyloxy-2,2,6,6-tetramethylpiperidin-4-yl)-epsilon-caprolactam

A solution of 1.17 ml (0.01 mole) of benzoyl chloride in 10 ml of tetrahydrofuran is added to a solution of 2.7 g (0.012 mole) of the hydroxyl compound prepared in Example 15 and 1.4 ml of triethylamine dissolved in 75 ml of tetrahydrofuran. The reaction mixture is stirred for three hours at 25° C. and then refluxed for ten minutes. The triethylammonium hydrochloride formed is removed by filtration. The solvent is then evaporated and the residue is recrystallized from ethanol: water to give 2.4 g of the above-named product as a solid melting at 154°–156° C.

IR ($CH_2Cl_2$) $\nu$ (C=O) 1730, 1621 $cm^{-1}$

Analysis $C_{22}H_{32}N_2O_3$ (372.49): Calc: C, 70.93; H, 8.66; N, 7.52. Found: C, 71.0; H, 8.7; N, 7.7.

EXAMPLE 17

1,2,2,6,6-Pentamethylpiperidin-4-yl 4-(2-Oxo-1-azepinyl)-2,2,6,6-tetramethylpiperidin-1-ylacetate (a) A mixture of 50.5 g (0.2 mole) of the lactam compound prepared in Example 1, 49.0 g (0.4 mole) of ethyl chloroacetate and 42.4 g (0.4 mole) of sodium carbonate in 100 ml of N,N-dimethylformamide (DMF) are heated for seven hours at 130° C. The unreacted ethyl chloroacetate is then removed in vacuo along with 40 ml of DMF. The concentrated residue is then diluted with 500 ml of ice water. The crude solid obtained is isolated by filtration, washed with water and dried. Recrystallization from heptane gives 47.5 g of a solid melting at 130°–134° C. identified by NMR as the desired intermediate ethyl 4-(2-oxo-1-azepinyl)-2,2,6,6-tetramethylpiperidin-1-ylacetate.

(b) A solution of 7.5 g (0.022 mole) of ethyl 4-(2-oxo-1-azepinyl)-2,2,6,6-tetramethylpiperidin-1-ylacetate and 4.2 g (0.024 mole) of 1,2,2,6,6-pentamethylpiperidin-4-ol in 50 ml of xylene is heated for one hour at 120° C. in the presence of 0.1 g of lithium amide esterification catalyst. The xylene-ethanol azeotropic mixture is slowly distilled off using an oil bath held at 150° C. to heat the reaction vessel. After five hours, four drops of acetic acid is added to the reaction mixture and the xylene solvent is removed by distillation.

The residue is recrystallized from heptane to give 6.1 g of the above-named compound as white crystals melting at 166°–168° C.

The structure of the compound is confirmed by the NMR spectrum.

Analysis $C_{27}H_{49}N_3O_3$ (463.7): Calc: C, 69.9; H, 10.7; N, 9.1. Found: C, 69.9; H, 10.4; N, 9.0.

EXAMPLE 18

1,6-Hexamethylene Bis[4-(2-oxo-1-azepinyl)-2,2,6,6-tetramethylpiperidin-1-ylacetate]

Following the procedure of Example 17(b), when two equivalents of ethyl 4-(2-oxo-1-azepinyl)-2,2,6,6-tetramethylpiperidin-1-ylacetate and one equivalent of 1,6-hexanediol, the above-named compound is obtained as a white crystalline solid melting at 147°–149° C.

Analysis $C_{40}H_{70}N_4O_6$ (703): Calc: C, 68.3; H, 10.0; N, 8.0. Found: C, 68.6; H, 9.8; N, 8.1.

EXAMPLE 19

1-Ethylene-2,2,6,6-tetramethylpiperidin-4-yl Bis[4-(2-oxo-1-azepinyl)-2,2,6,6-tetramethylpiperidin-1-ylacetate]

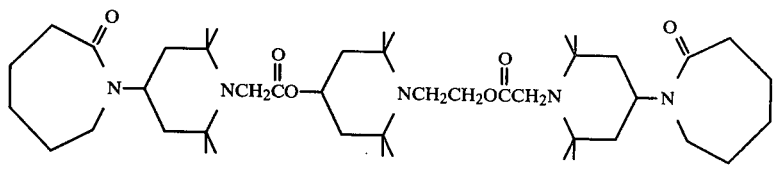

The above-named compound is prepared according to the procedure of Example 17(b) when one equivalent of 1-(2-hydroxyethyl)-2,2,6,6-tetramethylpiperidin-4-ol and two equivalents of ethyl 4-(2-oxo-1-azepinyl)-2,2,6,6-tetramethylpiperidin-1-ylacetate are reacted. The product is obtained as a white solid after recrystallization from toluene which melted at 228°–229° C.

Analysis $C_{45}H_{79}N_5O_6$ (786.1): Calc: C, 68.8; H, 10.1; N, 8.9. Found: C, 68.9; H, 9.9; N, 8.7.

EXAMPLE 20

Polypropylene (Hercules Profax 6501) containing a 0.1% by weight of calcium stearate, but no antioxidant, is blended with the instant light stabilizers. The mixture is pelletized and extruded at 450° F. (232° C.) into 4 inch (10.2 cm) tape with a thickness of 5 mil (0.127 mm). The tape is out cut into ¼ inch (6.4 mm) wide strips which are then stretched by a 6:1 ratio over Godet rolls at a temperature of 225° F. (107° C.) to give a stretched film tape of 2 mil (0.0508 mm) thickness.

The tape is subjected to light exposure in the carbon arc Weatherometer. After exposure, specimen tensile properties are determined with the hours to failure being taken as the time (hours) required for the tensile strength value to fall to 50% on the initial value.

The results are given in the table.

| Polypropylene plus 0.1% by weight light stabilizer of Example No. | Hours to Failure (50% Retention of Tenacity) Carbon Arc Weatherometer |
|---|---|
| no light stabilizer | 230 |
| 1 | 2430 |
| 3 | 2445 |
| 6 | 1800 |
| 7 | 1805 |
| 12 | 1880 |
| 13 | 1490 |

EXAMPLE 21

Weatherability of Thermoset Acrylic Resin Compositions

A thermoset acrylic enamel composition, used in automotive paint formulations, is stabilized as seen below by incorporation of the indicated stabilizer into the automotive paint. The stabilized composition is then sprayed over a primer on a metallic panel. The panel is then heated for 30 minutes at 120° C. to cure the composition. The initial coating film thickness is 1.5 mils (38 microns, 0.038 mm).

The panel is then subjected to the accelerated (quick) weathering test (QUV) involving alternating 4-hour period of UV irradiation at 60° C. with a 4-hour period of condensation (rain) at 50° C. for each cycle for a total of 3540 hours.

Gloss values (20° gloss) as measured by ASTM D-523 using a standard glossmeter or goniophotometer and Distinctness of Image (DI) (ASTM D-16), measured using a spectrophotometer, are measured on the coating surface before exposure and after exposure in the QUV test. The results are given in the table below and are expressed in % of the property retained after exposure.

| Stabilizer[a] (% by weight) | % Retention of Property after Exposure in QUV | |
|---|---|---|
| | 20° gloss | DI |
| none | b | b |
| Stabilizer A (2%) | 6 | 7 |
| Stabilizer A (2%) plus compound of Example 9 (1%) | 28 | 33 |

[a] Stabilizer A is 2-[2-hydroxy-3,5-di-(α,α-dimethylbenzyl)-phenyl]-2H—benzotriazole.
b. Coating without any stabilizer totally degraded after 1100 hour exposure in QUV.

The thermoset acrylic enamel is based on a binder of 70% of acrylic monomers such as hydroxyethyl acrylate, styrene, acrylonitrile, butyl acrylate and acrylic acid with 30% of a melamine resin.

EXAMPLE 22

0.5% by weight of an instant compound (as indicated below) is added as a stabilizer to the polymer (as indicated below) in the appropriate mixing equipment.

| Stabilizer of Example | Polymer |
|---|---|
| 4 | polystyrene |
| 11 | polyamide |
| 13 | polyurethane |
| 9 | poly(vinyl chloride) |

The stabilized composition is fabricated into a film or pellicle which is then exposed to actinic radiation. The stabilized film or pellicle retains desirable physical properties after exposure to UV light for a longer period than does a film or pellicle prepared from unstabilized polymer.

What is claimed is:

1. A light stabilizer compound of the formula I or II $$(L-T)_g-E \qquad (I)$$

or $$(L-T-G)_h-Q \qquad (II)$$

wherein
L is a lactam group of the formula

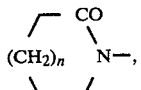

n is 0 to 3,
T is a group of the formula

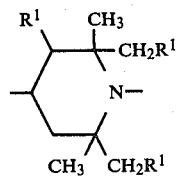

with
L attached to the 4-position of the piperidinyl ring,
$R^1$ is hydrogen or alkyl of 1 to 5 carbon atoms,
g is 1 or 2,
when g is 1,
E is hydrogen, oxygen, hydroxyl, alkyl of 1 to 12 carbon atoms, alkenyl with 3 to 8 carbon atoms, propargyl, benzyl, cyano, hydroxyalkyl of 2 to 4 carbon atoms, alkanoyl of 2 to 10 carbon atoms, alkenoyl of 3 to 4 carbon atoms, benzoyl, alkoxy of 1 to 8 carbon atoms, alkanoyloxy of 2 to 10 carbon atoms, alkenoyloxy of 3 to 4 carbon atoms, benzoyloxy,
when g is 2,
E is a straight- or branched-chain alkylene of 2 to 6 carbon atoms, styrolene, 2-butenylene or alkylenearylenealkylene of 8 to 15 carbon atoms; or
G is $G_1$ or $G_2$,
$G_1$ is

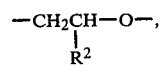

$R^2$ is hydrogen, alkyl of 1 to 2 carbon atoms or phenyl,
$G_2$ is $-CH_2COO-$,
where
T is attached to the methylene carbon atom of $G_1$ or $G_2$,
h is 1 to 4,
when h is 1 and G is $G_1$,
Q is alkanoyl of 2 to 10 carbon atoms, benzoyl, or the group

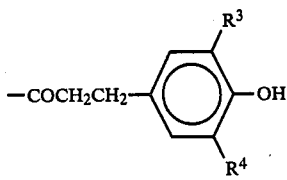

R³ is alkyl of 1 to 8 carbon atoms,
R⁴ is branched alkyl of 3 to 8 carbon atoms,
when h is 2 and G is G₁,
Q is carbonyl, oxalyl or alkanedioyl of 3 to 12 carbon atoms,
when h is 3 and G is G₁,
Q is alkanetrioyl of 6 to 10 carbon atoms,
when h is 4, and G is G₁
Q is alkanetetroyl of 8 to 12 carbon atoms,
when h is 1 and G is G₂,
Q is alkyl of 1 to 12 carbon atoms, or the group T—E where E is as defined above when g is 1,
when h is 2 and G is G₂,
Q is alkylene of 2 to 12 carbon atoms, cycloalkylene of 6 to 8 carbon atoms, 3-oxapentamethylene, 1,4-cyclohexylenedimethylene or the group —T—CH₂CH₂—,
when h is 3 and G is G₂,
Q is alkanetriyl of 3 to 8 carbon atoms, or
when h is 4 and G is G₂,
Q is alkanetetrayl of 4 to 10 carbon atoms.

2. A compound according to claim 1, where in the group L, n is 2 or 3.

3. A compound according to claim 2 wherein n is 2.

4. A compound according to claim 1, where in the group T, R¹ is hydrogen or methyl.

5. A compound according to claim 4 wherein R¹ is hydrogen.

6. A compound according to claim 1 wherein, when g is 1, E is hydrogen, oxygen, hydroxyl, alkyl of 1 to 4 carbon atoms, allyl, 2-hydroxyethyl, acetyl, propargyl, benzyl, cyano, benzoyl or benzoyloxy.

7. A compound according to claim 1 wherein, when g is 2, E is ethylene or p-xylylene.

8. A compound according to claim 1 wherein R² is hydrogen.

9. A compound according to claim 1 wherein, when h is 1 and G is G₁, Q is acetyl or the group

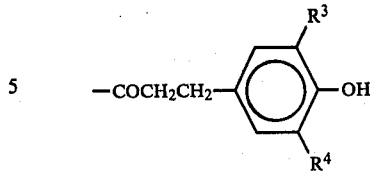

where R³ and R⁴ are each tert-butyl.

10. A compound according to claim 1 wherein, when h is 2 and G is G₁, Q is alkanedioyl of 6 to 10 carbon atoms.

11. A compound according to claim 1 wherein, when h is 1 and G is G₂, Q is alkyl of 1 to 4 carbon atoms or the group T—E as defined in claim 1.

12. A compound according to claim 1 wherein, when h is 2 and G is G₂, Q is alkylene of 2 to 8 carbon atoms or the group —T—CH₂CH₂—.

13. A compound according to claim 1 which is N-(2,2,6,6-tetramethylpiperidin-4-yl)-epsilon-caprolactam.

14. A compound according to claim 1 which is N-(1-allyl-2,2,6,6-tetramethylpiperidin-4-yl)-epsilon-caprolactam.

15. A compound according to claim 1 which is di-[2-[4-(2-oxo-1-azepinyl)-2,2,6,6-tetramethylpiperidin-1-yl]ethyl]sebacate.

16. A compound according to claim 1 which is 1,2,2,6,6-pentamethylpiperidin-4-yl 4-(2-oxo-1-azepinyl)-2,2,6,6-tetramethylpiperdin-1-ylacetate.

17. A compound according to claim 1 which is N-(1-acetyl-2,2,6,6-tetramethylpiperidin-4-yl)-epsilon-caprolactam.

18. A compound according to claim 1 which is N-(1-hydroxy-2,2,6,6-tetramethylpiperidin-4-yl)-epsilon-caprolactam.

19. A composition of matter comprising an organic material subject to light-induced deterioration stabilized with from 0.05 to 5% by weight of a compound according to claim 1.

20. A composition according to claim 19 in which the organic material is a polyolefin.

21. A composition according to claim 20 in which the polyolefin is polyethylene or polypropylene.

22. A composition according to claim 19 wherein the compound is N-(2,2,6,6-tetramethylpiperidin-4-yl)-epsilon-caprolactam.

23. A method of stabilizing an organic material subject to light-induced deterioration which comprises adding to said material from 0.05 to 5% by weight of a compound according to claim 1.

24. A method according to claim 23 in which the organic material is a polyolefin.

25. A method according to claim 24 in which the polyolefin is polyethylene or polypropylene.

26. A method according to claim 23 wherein the compound is N-(2,2,6,6-tetramethylpiperidin-4-yl)-epsilon-caprolactam.

* * * * *